US010493109B2

(12) United States Patent
Sun et al.

(10) Patent No.: US 10,493,109 B2
(45) Date of Patent: *Dec. 3, 2019

(54) LITHIUM STIMULATION OF CORD BLOOD STEM CELL PROLIFERATION AND GROWTH FACTOR PRODUCTION

(71) Applicant: RUTGERS, THE STATE UNIVERSITY OF NEW JERSEY, New Brunswick, NJ (US)

(72) Inventors: Dongming Sun, Piscataway, NJ (US); Wise Young, New Brunswick, NJ (US)

(73) Assignee: RUTGERS, THE STATE UNIVERSITY OF NEW JERSEY, New Brunswick, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/782,652

(22) Filed: Oct. 12, 2017

(65) Prior Publication Data
US 2018/0250344 A1    Sep. 6, 2018

Related U.S. Application Data

(63) Continuation of application No. 14/493,243, filed on Sep. 22, 2014, now abandoned, which is a continuation of application No. 12/513,331, filed as application No. PCT/US2007/083210 on Oct. 7, 2007, now Pat. No. 8,852,938.

(60) Provisional application No. 60/856,071, filed on Nov. 1, 2006.

(51) Int. Cl.
*A61K 35/51* (2015.01)
*C12N 5/0775* (2010.01)
*A61K 33/00* (2006.01)
*A61K 35/50* (2015.01)
*C12N 5/0789* (2010.01)
*C12N 5/073* (2010.01)

(52) U.S. Cl.
CPC .............. *A61K 35/51* (2013.01); *A61K 33/00* (2013.01); *A61K 35/50* (2013.01); *C12N 5/0605* (2013.01); *C12N 5/0647* (2013.01); *C12N 5/0665* (2013.01); *C12N 2500/12* (2013.01)

(58) Field of Classification Search
CPC ...... A61K 35/51; A61K 33/00; C12N 5/0605; C12N 5/0665; C12N 5/0647; C12N 2500/12
See application file for complete search history.

(56) References Cited

U.S. PATENT DOCUMENTS

| 8,852,938 B2 | 10/2014 | Sun et al. |
| 2002/0001826 A1 | 1/2002 | Wager et al. |
| 2006/0147435 A1* | 7/2006 | Moon .................. A61K 48/005 424/93.21 |

FOREIGN PATENT DOCUMENTS

| WO | 2000/006700 A1 | 2/2000 |
| WO | WO 2004/094610 | * 11/2004 |
| WO | 2004/113513 A2 | 12/2004 |

OTHER PUBLICATIONS

Gallicchio et al, Experimental Hematology, 1981, vol. 9, No. 7, pp. 804-810. (Year: 1981).*
Hordyjewska et al, Cytotechnology, 2015, vol. 67, pp. 387-396. (Year: 2015).*
Stambolic et al, Current Biology, 1996, vol. 6, No. 12, pp. 1664-1668. (Year: 1996).*
Zhao et al, Cell Transplantation, 2004, vol. 13, pp. 113-122. (Year: 2004).*
Almici et al., "Clonogenic capacity and ex vivo expansion potential of umbilical cord blood progenitor cells are not impaired by cryopreservation," Bone Marrow Transplant, 1997, vol. 19, pp. 1079-1084.
Austin et al., "A role for the Wnt gene family in hematopoiesis: expansion of multilineage progenitor cells," Blood, 1997, vol. 89, pp. 3624-3635.
Chang, Y. et al., "Disparate mesenchyme-lineage tendencies in mesenchymal stem cells from human bone marrow and umbilical cord blood," Stem Cells, 24:679-685, 2006.
De Boer et al., "Wnt signaling inhibits osteogenic differentiation of human mesenchymal stem cells," Bone, 2004, vol. 34, pp. 818-826.
Holmes et al., "Glycogen synthase kinase-3β 3 inhibition preserves hematopoietic stem cell activity and inhibits leukemic cell growth," Stem Cells, 2008, vol. 26, pp. 1288-1297.
*Igaku no Ayumi* (Journal of Clinical and Experimental Medicine), 2000, vol. 194, No. 4, pp. 1143-1147.
Jope, R., "Anti-bipolar therapy: mechanism of action of lithium," Molecular Psychiatry, 4:117-128, 1999.
Kern, S. et al., "Comparative analysis of mesenchymal stem cells from bone marrow, umbilical cord blood, or adipose tissue," Stem Cells, 24:1294-1301, 2006.
Kuwabara, "Effects of lithium on mouse hematopoiesis," *Nippon Ika Daigaku Zasshi* (Journal of Nippon Medical School), 1990, vol. 57, No. 5, pp. 408-415.
Lee, M. et al., "Isolation of mesenchymal stem cells from cryopreserved human umbilical cord blood," International Journal of Hematology, 81:126-130, 2005.

(Continued)

*Primary Examiner* — Allison M Fox
(74) *Attorney, Agent, or Firm* — Kilpatrick Townsend & Stockton LLP

(57) ABSTRACT

The present invention provides methods for expanding human umbilical cord blood stem cells and methods for stimulating growth factor production by cord blood stem cells using an in vitro cell culture system comprising a lithium salt. The present invention also provides in vivo methods for enhancing the survival and growth of transplanted cord blood stem cells by treating the cells with a lithium salt prior to transplantation. In vivo methods for reducing rejection of transplanted cord blood stem cells by administering a lithium salt after transplantation are also provided.

6 Claims, 10 Drawing Sheets

(56) References Cited

OTHER PUBLICATIONS

Lu, "Characterization of Cord Blood Stem/Progenitor Cells (High Proliferative Potential Colony-Forming Cells)," Journal of Hematotherapy, 1993, vol. 2, pp. 201-202.

McGrath et al., "Lithium Stimulation of HPP-CFC and Stromal Growth Factor Production in Murine Dexter Culture," J. Cell. Physiol, 1992, vol. 151, pp. 276-286.

Neth, P. et al., "Wnt signaling regulates the invasion capacity of human mesenchymal cells," Stem Cells, 24:1892-1903, 2006.

Newport, D. et al., "Lithium placental passage and obstetrical outcome: implications for clinical management during late pregnancy," Am. J. Psychiatry, 162:2162-2170, 2005.

Reya et al., "A role for Wnt signaling in self-renewal of haematopoietic stem cells," Nature, May 22, 2003, vol. 423, pp. 409-414.

Tsai, M. et al., "Functional network analysis of the transcriptomes of mesenchymal stem cells derived from amniotic fluid, amniotic membrane, cord blood, and bone marrow," Stem Cells, 25:2511-2523, 2007.

Van Der Heyden, M. et al., "Twenty one years of P19 cells: what an embryonal carcinoma cell line taught us about cardiomyocyte differentiation," Cardiovascular Research, 58:292-302, 2003.

Wagner, W. et al., "Comparative characteristics of mesenchymal stem cells from human bone marrow, adipose tissue, and umbilical cord blood," Experimental Hematology, 33:1402-1416, 2005.

\* cited by examiner

LITHIUM STIMULATION OF CORD BLOOD STEM CELL PROLIFERATION AND GROWTH FACTOR PRODUCTION

CROSS-REFERENCES TO RELATED APPLICATIONS

The present application is a continuation of U.S. patent application Ser. No. 14/493,243, filed Sep. 22, 2014, which is a continuation of U.S. patent application Ser. No. 12/513,331, filed Apr. 7, 2010, which application issued on Oct. 7, 2014 as U.S. Pat. No. 8,852,938 B2, which is a national phase application of PCT/US2007/083210, filed Oct. 31, 2007, which application claims priority to U.S. Provisional Application No. 60/856,071, filed Nov. 1, 2006, the disclosures of which are herein incorporated by reference in their entireties for all purposes.

BACKGROUND OF THE INVENTION

There is considerable interest in the identification, isolation, and generation of human stem cells. Human stem cells are typically totipotential or pluripotential precursor cells capable of self-renewal and generating a variety of mature human cell lineages. This ability serves as the basis for the cellular differentiation and specialization necessary for organ and tissue development. Recent success at transplanting stem cells have provided new clinical tools to reconstitute and/or supplement bone marrow after myeloablation due to disease, exposure to toxic chemicals, and/or radiation. Further evidence exists that demonstrates that stem cells can be employed to repopulate many, if not all, tissues and restore physiologic and anatomic functionality.

Many different types of mammalian stem cells have been characterized. For example, embryonic stem cells, embryonic germ cells, adult stem cells, and other committed stem cells or progenitor cells are known. In fact, certain stem cells have not only been isolated and characterized, but have also been cultured under conditions to allow a limited degree of differentiation. Because of the tens of millions of possible combinations of HLA types in the population, a basic problem remains, in that it is very difficult to obtain sufficient quantities, populations, and varieties of HLA types of human stem cells which are capable of differentiating into all cell types that can be HLA matched to individual patients. Stem cells of different HLA types are in critically short supply. Due to their importance in the treatment of a wide variety of diseases and conditions, including malignancies, inborn errors of metabolism, hemoglobinopathies, and immunodeficiencies, it would be highly advantageous to have an adequate source of stem cells of various HLA types.

Obtaining sufficient numbers of human stem cells has been problematic for several reasons. First, isolation of normally occurring populations of stem cells in adult tissues has been technically difficult and costly due, in part, to very limited quantities found in blood or tissue. Second, procurement of these cells from embryos or fetal tissue, including aborted fetuses, has raised ethical concerns. Alternative sources that do not require the use of cells procured from embryonic or fetal tissue are therefore essential for further progress in the clinical use of stem cells. There are, however, few viable alternative sources of stem cells, particularly human stem cells, and thus the supply is limited. Furthermore, harvesting of stem cells from alternative sources in adequate amounts for therapeutic and research purposes is generally laborious.

For example, U.S. Pat. No. 5,486,359 discloses human mesenchymal stem cell (HMSC) compositions derived from bone marrow. Homogeneous HMSC compositions are obtained by positive selection of adherent marrow or periosteal cells that are free of markers associated with either hematopoietic cells or differentiated mesenchymal cells. The isolated mesenchymal cell populations display characteristics associated with mesenchymal stem cells, have the ability to regenerate in culture without differentiating, and have the ability to differentiate into specific mesenchymal lineages when either induced in vitro or placed in vivo at the site of damaged tissue. The drawback of such methods, however, is that they first require the invasive and painful harvesting of marrow or periosteal cells from a human donor in order to subsequently isolate HMSCs.

Umbilical cord blood is a known alternative source of mesenchymal stem cells as well as hematopoietic stem cells and progenitor cells. Stem cells from cord blood are routinely cryopreserved for hematopoietic reconstitution, a therapeutic procedure used in bone marrow and other related transplantations (see, e.g., U.S. Pat. Nos. 5,004,681 and 5,192,553). Conventional techniques for the collection of cord blood are based on the use of a needle or cannula, which is used with the aid of gravity to drain cord blood from the placenta (see, e.g., U.S. Pat. Nos. 5,004,681, 5,192,553, 5,372,581, and 5,415,665). The needle or cannula is usually placed in the umbilical vein and the placenta is gently massaged to aid in draining cord blood from the placenta. A major limitation of stem cell procurement from cord blood, however, has been the frequently inadequate volume of cord blood obtained, resulting in insufficient cell numbers to effectively reconstitute bone marrow after transplantation.

Stem cells have the potential to be used in the treatment of a wide variety of diseases and injuries, including nervous system trauma (e.g., spinal cord injury), malignancies, genetic diseases, hemoglobinopathies, and immunodeficiencies. However, stem cells from umbilical cord blood are in critically short supply due to restrictions on their collection, the inadequate numbers of cells typically collected from cord blood, especially if used to treat an adult patient, and the extraordinary cost of establishing a large inventory. As such, there is a strong need in the art for methods of culturing cord blood stem cells in a cell culture system capable of expanding stem cells to a number sufficient for transplantation. There is also a need in the art for methods of enhancing the growth and survival of transplanted stem cells and reducing or delaying stem cell rejection in a recipient. The present invention satisfies these and other needs.

SUMMARY OF THE INVENTION

The present invention provides methods for stimulating growth factor production by human umbilical cord blood stem cells and methods for expanding cord blood stem cells using an in vitro cell culture system comprising a lithium salt. The present invention also provides in vivo methods for enhancing the survival and growth of transplanted cord blood stem cells by treating the cells with a lithium salt prior to transplantation. The present invention further provides in vivo methods for reducing rejection of transplanted cord blood stem cells by administering a lithium salt after transplantation.

The present invention is based, in part, on the surprising discovery that lithium stimulates the production or expression of growth factors by stem cells. Without being bound to any particular theory, the effect of lithium on stem cell proliferation, survival, and immune rejection is mediated by the amount of growth factors that stem cells produce or express in response to a lithium salt.

As such, in one aspect, the present invention provides a method for stimulating growth factor production by human umbilical cord blood cells, the method comprising culturing the cells in a medium comprising a lithium salt.

Lithium typically stimulates the production or expression of growth factors such as cell survival factors, anti-differentiation factors, and combinations thereof. Examples of cell survival factors include, but are not limited to, neurotrophins, cytokines, epidermal growth factor (EGF), platelet-derived growth factor (PDGF), fibroblast growth factor (FGF), insulin-like growth factor (IGF), heparin-binding epidermal growth factor (HB-EGF), vascular endothelial growth factor (VEGF), pigment epithelium-derived factor (PEDF), schwannoma-derived growth factor (SDGF), hepatocyte growth factor (HGF), transforming growth factor-$\alpha$ (TGF-$\alpha$), transforming growth factor-$\beta$ (TGF-$\beta$), bone morphogenetic proteins (e.g., BMP1-BMP15), growth differentiation factor-9 (GDF-9), granulocyte-colony stimulating factor (G-CSF), granulocyte-macrophage colony stimulating factor (GM-CSF), myostatin (GDF-8), erythropoietin (EPO), thrombopoietin (TPO), and combinations thereof. Leukemia inhibitory factor (LIF) is a preferred anti-differentiation factor.

Examples of neurotrophins include, without limitation, neurotrophin-1 (NT-1), neurotrophin-3 (NT-3), neurotrophin-4 (NT-4), brain-derived neurotrophic factor (BDNF), glial-derived neurotrophic factor (GDNF), ciliary neurotrophic factor (CNTF), nerve growth factor (NGF), and combinations thereof.

Non-limiting examples of cytokines include IL-1$\alpha$, IL-1$\beta$, IL-2, IL-4, IL-5, IL-6, IL-7, IL-8, IL-9, IL-10, IL-12, IL-13, IL-15, IL-17, IL-23, IL-27, TNF-$\alpha$, IFN-$\alpha$, IFN-$\beta$, IFN-$\gamma$, CXCL1/GRO1/GRO$\alpha$, CXCL2/GRO2, CXCL3/GRO3, CXCL4/PF-4, CXCL5/ENA-78, CXCL6/GCP-2, CXCL7/NAP-2, CXCL9/MIG, CXCL10/IP-10, CXCL11/I-TAC, CXCL12/SDF-1, CXCL13/BCA-1, CXCL14/BRAK, CXCL15, CXCL16, CXCL17/DMC, CCL1, CCL2/MCP-1, CCL3/MIP-1$\alpha$, CCL4/MIP-1$\beta$, CCL5/RANTES, CCL6/C10, CCL7/MCP-3, CCL8/MCP-2, CCL9/CCL10, CCL11/Eotaxin, CCL12/MCP-5, CCL13/MCP-4, CCL14/HCC-1, CCL15/MIP-5, CCL16/LEC, CCL17/TARC, CCL18/MIP-4, CCL19/MIP-3$\beta$, CCL20/MIP-3$\alpha$, CCL21/SLC, CCL22/MDC, CCL23/MPIF1, CCL24/Eotaxin-2, CCL25/TECK, CCL26/Eotaxin-3, CCL27/CTACK, CCL28/MEC, CL1, CL2, CX$_3$CL1, and combinations thereof.

Examples of lithium salts suitable for use in the methods of the present invention include, but are not limited to, lithium chloride, lithium carbonate, and lithium sulfate. Preferably, the lithium salt is lithium chloride. In some embodiments, the lithium salt, e.g., lithium chloride, is present in the cell culture medium at a concentration of from about 0.5 to about 5 mM, e.g., about 0.5, 1, 1.5, 2, 2.5, 2.6, 2.7, 2.8, 2.9, 3, 3.1, 3.2, 3.3, 3.4, 3.5, 4, 4.5, or 5 mM. In a preferred embodiment, the lithium salt is present in the cell culture medium at a concentration of about 3 mM.

In certain instances, the cord blood cells can be cultured with a lithium mimetic compound (see, e.g., Gould et al., *Neuropsychopharmacology*, 30:1223-1237 (2005); and Gould, *Expert Opin. Ther. Targets*, 10:377-392 (2006)). In certain other instances, the cord blood cells can be cultured with a psychotropic drug similar to lithium such as, for example, valproic acid (see, e.g., Hahn et al., *J. Psychiatr. Res.*, 39:355-363 (2005); Shao et al., *Biol. Psychiatry*, 58:879-884 (2005); and Dokucu et al., *Neuropsychopharmacology*, 30:2216-2224 (2005)), disodium valproate (see, e.g., Calabrese et al., *Am. J. Psychiatry*, 162:2152-2161 (2005)), and carbamazepine (see, e.g., Bazinet et al., *Biol. Psychiatry*, 59:401-407 (2006)).

In some embodiments, a collected cord blood unit is first substantially depleted of plasma and the stem cells present in the plasma-depleted cord blood unit are then cultured with a lithium salt. In other embodiments, a collected cord blood unit is first substantially depleted of red blood cells and the stem cells present in the red blood cell-depleted cord blood unit are then cultured with a lithium salt. The cord blood stem cells can be cultured in a medium comprising a lithium salt using any in vitro culture technique known to one skilled in the art either before or after cryopreservation of the plasma-depleted or red blood cell-depleted cord blood unit.

In another aspect, the present invention provides a method for expanding human umbilical cord blood cells, the method comprising culturing the cells in a medium comprising a lithium salt.

Examples of suitable lithium salts include, but are not limited to, lithium chloride, lithium carbonate, and lithium sulfate. Preferably, the lithium salt is lithium chloride. In some embodiments, the lithium salt, e.g., lithium chloride, is present in the cell culture medium at a concentration of from about 0.5 to about 5 mM, e.g., about 0.5, 1, 1.5, 2, 2.5, 2.6, 2.7, 2.8, 2.9, 3, 3.1, 3.2, 3.3, 3.4, 3.5, 4, 4.5, or 5 mM. In a preferred embodiment, the lithium salt is present in the cell culture medium at a concentration of about 3 mM.

In certain instances, the cord blood cells can be cultured with a lithium mimetic compound. In certain other instances, the cord blood cells can be cultured with a psychotropic drug similar to lithium such as, for example, valproic acid, disodium valproate, carbamazepine, and combinations thereof.

As described above, a collected cord blood unit can be substantially depleted of plasma and the stem cells present in the plasma-depleted cord blood unit can then be cultured with a lithium salt. Alternatively, a collected cord blood unit can be substantially depleted of red blood cells and the stem cells present in the red blood cell-depleted cord blood unit can then be cultured with a lithium salt. The cord blood stem cells can be cultured in a medium comprising a lithium salt using any suitable in vitro culture technique known in the art either before or after cryopreservation of the plasma-depleted or red blood cell-depleted cord blood unit.

In yet another aspect, the present invention provides a method for enhancing the survival and growth of transplanted human umbilical cord blood cells in a subject, the method comprising: (a) culturing the cells in a medium comprising a lithium salt; and (b) administering the cells of step (a) to the subject.

Examples of lithium salts suitable for use in the methods of the present invention for enhancing the survival and growth of transplanted cord blood cells include, but are not limited to, lithium chloride, lithium carbonate, and lithium sulfate. Preferably, the lithium salt is lithium chloride. In some embodiments, the lithium salt, e.g., lithium chloride, is present in the cell culture medium at a concentration of from about 0.5 to about 5 mM, e.g., about 0.5, 1, 1.5, 2, 2.5, 2.6, 2.7, 2.8, 2.9, 3, 3.1, 3.2, 3.3, 3.4, 3.5, 4, 4.5, or 5 mM. In a preferred embodiment, the lithium salt is present in the cell culture medium at a concentration of about 3 mM.

In certain instances, the cord blood cells can be cultured with a lithium mimetic compound. Alternatively, the cord blood cells can be cultured with a psychotropic drug similar to lithium such as, for example, valproic acid, disodium valproate, carbamazepine, and combinations thereof.

As described above, a collected cord blood unit can be substantially depleted of plasma and the stem cells present in the plasma-depleted cord blood unit can then be cultured with a lithium salt. Alternatively, a collected cord blood unit can be substantially depleted of red blood cells and the stem cells present in the red blood cell-depleted cord blood unit can then be cultured with a lithium salt. The cord blood stem cells can be cultured in a medium comprising a lithium salt using any suitable in vitro culture technique known in the art either before or after cryopreservation of the plasma-depleted or red blood cell-depleted cord blood unit.

The subject is typically a mammal such as a human. In instances where the subject has been diagnosed with an injury such as a spinal cord injury, the cultured cells are preferably administered intraspinally.

In certain instances, the method further comprises administering a lithium salt such as lithium chloride to the subject, e.g., a mammal such as a human. The lithium salt, e.g., lithium chloride, is usually administered by a route including, but not limited to, oral, intrathecal, intraventricular, subcutaneous, intraperitoneal, intravenous, and intramuscular. In some embodiments, the lithium salt is administered to the subject at a dose of from about 1 mg/kg to about 150 mg/kg, e.g., about 1, 5, 6, 7, 8, 9, 10, 11, 12, 13, 14, 15, 20, 25, 50, 75, 100, 125, or 150 mg/kg. In a preferred embodiment, the lithium salt is administered at a dose of about 10 mg/kg.

The cultured cells and lithium salts of the present invention can be administered either alone or in a mixture with a pharmaceutically acceptable carrier selected in accordance with the route of administration and standard pharmaceutical practice. As a non-limiting example, normal buffered saline (e.g., about 135-150 mM NaCl) can be employed as the pharmaceutically acceptable carrier. Other suitable carriers include, but are not limited to, water, buffered water, 0.4% saline, 0.3% glycine, and the like. Additional carriers suitable for use in delivering the cultured stem cells and lithium salts of the present invention are described in, e.g., REMINGTON'S PHARMACEUTICAL SCIENCES, Mack Publishing Co., Philadelphia, Pa., 18th ed. (1995).

In a further aspect, the present invention provides a method for reducing rejection of transplanted human umbilical cord blood cells in a subject, the method comprising administering a lithium salt to the subject after cell transplantation.

The subject is typically a mammal such as a human. In instances where the subject has been diagnosed with an injury such as a spinal cord injury, the cells are preferably transplanted via intraspinal administration.

Non-limiting examples of lithium salts suitable for use in the methods of the present invention include lithium chloride, lithium carbonate, and lithium sulfate. Preferably, the lithium salt is lithium chloride. In certain instances, cord blood stem cells can be expanded using an in vitro culture technique in a medium comprising a lithium salt prior to cell transplantation. The cord blood stem cells can be obtained from a collected cord blood unit that is substantially depleted of plasma and/or red blood cells.

The lithium salt, e.g., lithium chloride, is usually administered by a route including, but not limited to, oral, intrathecal, intraventricular, subcutaneous, intraperitoneal, intravenous, and intramuscular. In some embodiments, the lithium salt is administered to the subject at a dose of from about 1 mg/kg to about 150 mg/kg, e.g., about 1, 5, 6, 7, 8, 9, 10, 11, 12, 13, 14, 15, 20, 25, 50, 75, 100, 125, or 150 mg/kg. In a preferred embodiment, the lithium salt is administered at a dose of about 10 mg/kg. In certain instances, a lithium mimetic compound or a psychotropic drug similar to lithium (e.g., valproic acid, disodium valproate, and/or carbamazepine) can be administered to the subject to reduce rejection of the transplanted cord blood stem cells.

The lithium salt described herein can be administered either alone or in a mixture with a pharmaceutically acceptable carrier selected in accordance with the route of administration and standard pharmaceutical practice. As a non-limiting example, normal buffered saline (e.g., about 135-150 mM NaCl) can be employed as the pharmaceutically acceptable carrier. Other suitable carriers include, but are not limited to, water, buffered water, 0.4% saline, 0.3% glycine, and the like. Additional carriers suitable for use in delivering the lithium salts of the present invention are described in, e.g., REMINGTON'S PHARMACEUTICAL SCIENCES, Mack Publishing Co., Philadelphia, Pa., 18th ed. (1995).

The lithium salt can be administered to the subject minutes, hours, days, weeks, months, and/or years after cell transplantation. In some embodiments, the subject can be treated with a second, third, fourth, fifth, sixth, seventh, eighth, ninth, tenth, or more dose of the same or different lithium salt after cell transplantation. In certain instances, one or more doses of the lithium salt can also be administered to the subject before and/or during cell transplantation.

Other features, objects, and advantages of the present invention and its preferred embodiments will become apparent from the detailed description, examples, and claims that follow.

DETAILED DESCRIPTION OF THE INVENTION

I. Introduction

Figure 1:
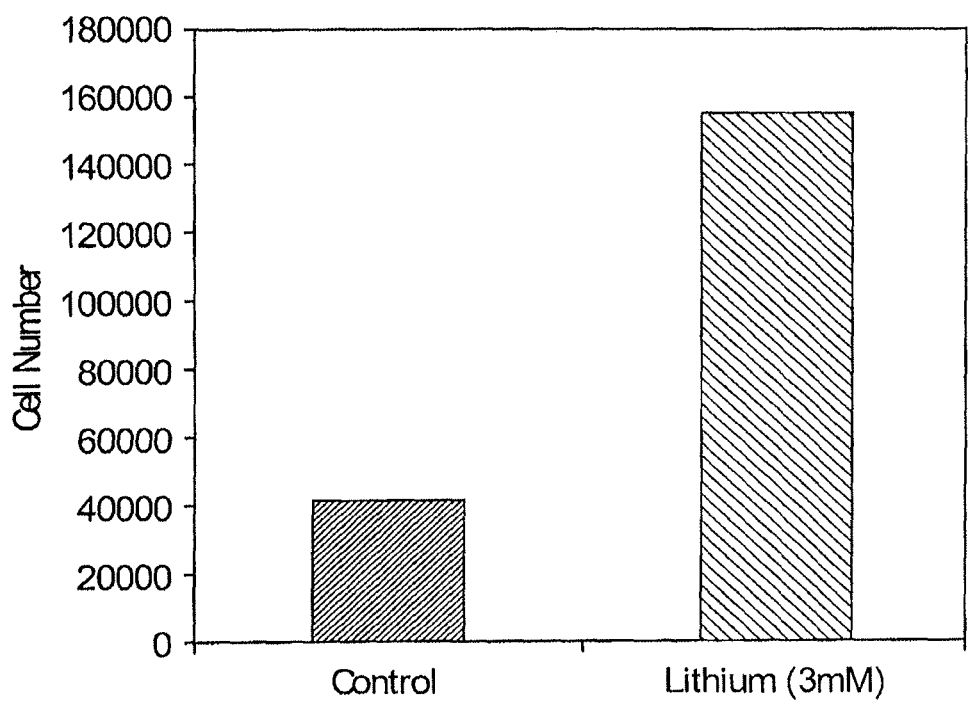
FIG. 1 illustrates data demonstrating that lithium promotes N01.1 cell proliferation in vitro.

Lithium has been used for over 50 years to treat bipolar disorder and other neurological conditions (see, e.g., Manji et al., *Biol. Psychiatry*, 46:929-940 (1999)). People with manic depression often take lithium for a lifetime, with therapeutic blood concentrations of about 1 mM. Despite such high concentrations, lithium is relatively non-toxic. Lithium has many potential mechanisms of action on cells (Jope, *Mol. Psychiatry,* 4:117-128 (1999)). For example, lithium modulates the activities of multiple enzymes including GSK-3, Akt, cAMP-dependent kinase, and protein kinase C, as well as their attendant second messengers and transcription factors.

Studies on the effects of lithium on neural cells have shown that lithium may stimulate neural regeneration (Bustuoabad et al., *Medicina,* 40:547-552 (1980)) and neural progenitor proliferation (Hashimoto et al., *Neuroscience,* 117:55-61 (2003)), induce proliferation of neuronal and astroglial cells near the injury site in stroke models (Chuang, *Crit. Rev. Neurobiol.,* 16:83-90 (2004)), enhance the proliferation of glial cells in the pituitary gland (Levine et al., *Cell Prolif,* 35:167-172 (2002); Levine et al., *Cell Prolif.,* 33:203-207 (2000)), stimulate the ability of white blood cells to migrate (Azzara et al., *Haematologica,* 72:121-127 (1987); Azzara et al., *Acta Haematol.,* 85:100-102 (1991)), increase neuronal differentiation of hippocampal neural progenitor cells (Kim et al., *J. Neurochem.,* 89:324-336 (2004)), and enhance neurogenesis in mouse hippocampus (Laeng et al., *J. Neurochem.,* 91:238-251 (2004)). However, none of these references considers the in vitro and in vivo effects of lithium on growth factor production by human umbilical cord blood stem cells. Likewise, these references fail to appreciate the in vitro and in vivo effects of lithium on human umbilical cord blood stem cell proliferation and survival.

Additionally, studies on the effects of lithium on bone marrow have shown that lithium may increase colony stimulating activity production and accelerate granulopoiesis and erythropoiesis (Labedzki et al., *Klin. Wochenschr.,* 58:211-218 (1980)), reduce chemotherapy-induced suppression of granulpoiesis and megacariopoiesis (Korycka et al., *Arch. Immunol. Ther. Exp.,* 39:501-509 (1991)), accelerate marrow recovery following total body irradiation (Johnke et al., *Int. J. Cell Cloning,* 9:78-88 (1991)), reverse marrow hypoplasia and pancytopenia caused by simultaneous administration of estradiol cyclopentylpropionate and diethylstilbestrol (Hall, *J. Am. Vet. Med. Assoc.,* 200:814-816 (1992)), and restore normal blood counts in patients with clozapine-induced granulocytopenia (Papetti et al., *Encephale.,* 30:578-582 (2004)). However, none of these references considers the in vitro and in vivo effects of lithium on growth factor production by human umbilical cord blood stem cells. Similarly, these references fail to appreciate the in vitro and in vivo effects of lithium on human umbilical cord blood stem cell proliferation and survival.

Accordingly, the present invention is based, in part, on the surprising discovery that culturing human umbilical cord blood stem cells in media containing a lithium salt such as lithium chloride can stimulate the production of growth factors by these stem cells, thereby promoting their proliferation and survival. In fact, culturing cord blood stem cells according to the methods of the present invention increases the amount of growth factor expression and the number of stem cells by several fold (e.g., at least 2, 3, 4, 5, 6, 7, 8, 9, or 10-fold). The present invention is also based on the surprising discovery that treating cord blood stem cells with a lithium salt prior to transplantation enhances the survival and growth of transplanted stem cells, and administering a lithium salt after cord blood stem cell transplantation reduces immune rejection of transplanted stem cells. As such, the methods described herein not only permit a substantial expansion of the limited supply of stem cells found in cord blood, but also provide a significant improvement in the clinical outcome of the transplant recipient, e.g., by increasing survival and growth of transplanted stem cells and/or decreasing immune rejection of transplanted stem cells.

II. Definitions

As used herein, the following terms have the meanings ascribed to them unless specified otherwise.

The term "stem cell" refers to any cell that has the ability to divide for indefinite periods of time and to give rise to specialized cells. Stem cells emanate from all germinal layers (i.e., ectoderm, mesoderm, and endoderm). Typical sources of stem cells include embryos, bone marrow, peripheral blood, umbilical cord blood, placental blood, muscle tissue, and adipose tissue. Stem cells can be totipotent, meaning that they are capable of growing and differentiating into any cell in the body. In mammals, only the zygote and early embryonic cells are totipotent. Alternatively, stem cells can be pluripotent, meaning that they are capable of generating most tissues in an organism. For example, pluripotent stem cells can give rise to cells of the nervous system, skin, liver, kidney, blood, muscle, bone, etc. Examples of pluripotent stem cells include, but are not limited to, cord blood stem cells, neural stem cells, hematopoietic stem cells, adipose-derived stem cells, mesenchymal stem cells, placentally-derived stem cells, exfoliated tooth-derived stem cells, and hair follicle stem cells. In contrast, multipotent or adult stem cells typically give rise to limited types of cells. The term stem cell as used herein includes progenitor cells unless otherwise noted.

The term "progenitor cell" refers to cells that are lineage-committed, i.e., an individual cell can give rise to progeny limited to a single lineage. Non-limiting examples of progenitor cells include precursor cells for the neuronal, hepatic, nephrogenic, adipogenic, osteoblastic, osteoclastic, alveolar, cardiac, intestinal, or endothelial lineage.

The term "culturing" as used herein refers to maintaining stem cells under conditions in which they can proliferate and avoid senescence. For example, in the present invention, stem cells are cultured in media containing a lithium salt and optionally one or more growth factors, i.e., a growth factor cocktail.

The term "stimulating growth factor production" refers to the use of a lithium salt to increase the expression (e.g., mRNA, protein) of one or more growth factors from stem cells. Typically, the increase in growth factor expression is compared to control stem cells that were cultured in the absence of a lithium salt. As described in Examples 1 and 2, the methods of the present invention can significantly stimulate the production of growth factors from stem cells, i.e., when stem cells are cultured in media containing a lithium salt. Examples of growth factors that can be stimulated by culturing stem cells with a lithium salt include, but are not limited to, cell survival factors (e.g., neurotrophins, cytokines, epidermal growth factor (EGF), platelet-derived growth factor (PDGF), fibroblast growth factor (FGF), insulin-like growth factor (IGF), etc.), anti-differentiation factors (e.g., leukemia inhibitory factor (LIF), etc.), and combinations thereof. Non-limiting examples of neurotrophins include neurotrophin-1 (NT-1), neurotrophin-3 (NT-3), neurotrophin-4 (NT-4), brain-derived neurotrophic factor (BDNF), glial-derived neurotrophic factor (GDNF), ciliary neurotrophic factor (CNTF), nerve growth factor (NGF) (e.g., NGFα, NGFβ, and NGFγ), and combinations thereof.

Examples of cytokines include those belonging to the interleukin or interferon subfamilies such as those described above.

The term "in vitro expansion" refers to the cultivation of stem cells in the laboratory. Such cells can be extracted from a mammal and additional quantities of cells generated by cultivation in the appropriate environment, e.g., in media containing a lithium salt. If possible, stable cell lines are established to allow for continued propagation of cells. As described in Examples 1 and 2, the methods of the present invention can significantly promote stem cell proliferation in vitro, i.e., when stem cells are cultured in media containing a lithium salt.

The term "enhancing survival and growth" refers to the use of a lithium salt to promote the viability and proliferation of transplanted stem cells. Typically, the enhancement in survival and growth of transplanted stem cells is compared to control stem cells that were cultured and transplanted in the absence of a lithium salt. As described in Example 1, the methods of the present invention can significantly enhance the survival and growth of transplanted stem cells, i.e., when lithium-treated stem cells are administered to a mammal. Viable cells are cells that are alive and frequently are capable of growth and division. Those of skill in the art are aware of methods to determine the viability of cells, e.g., by the ability to exclude trypan blue dye.

The term "reducing rejection" refers to the use of a lithium salt to reduce, delay, or abrogate the risk of immune rejection of transplanted stem cells. Typically, the reduction in rejection of transplanted stem cells is compared to control stem cells that were cultured and transplanted in the absence of a lithium salt. As a non-limiting example, the methods of the present invention can significantly delay the onset of immune rejection of transplanted stem cells when a lithium salt such as lithium chloride is administered to a stem cell recipient.

The term "umbilical cord blood" refers to a source of pluripotent and multipotent stem cells obtained from the blood of umbilical cords that are left over after birth. Examples of stem cells found in umbilical cord blood include, but are not limited to, mesenchymal stem cells, hematopoietic stem cells, and progenitor cells. Mesenchymal stem cells and progenitor cells can typically differentiate into nerve cells, marrow stromal cells, chondrocytes, osteoblasts, adipocytes, myocytes, tenocytes, and ligament cells. Hematopoietic stem cells can typically give rise to cells of the lymphoid, myeloid, and erythroid lineages. A detailed description of methods for collecting and processing cord blood is provided below.

The term "umbilical cord blood unit" as used herein refers to a volume of cord blood that is collected from a single donor. A single umbilical cord blood unit is typically used in the methods of the present invention, but multiple cord blood units, e.g., double cord blood units, can also be used to increase stem cell number.

As used herein, the terms "plasma is substantially depleted" and "plasma-depleted" refer to processed umbilical cord blood units in which a volume of plasma greater than about 30%, 35%, 40%, 45%, 50%, 55%, 60%, 65%, 70%, 75%, 80%, 85%, 90%, or 95% has been removed. For example, plasma can be substantially depleted by centrifuging cord blood and separating the cellular fraction from the plasma fraction. The plasma volume remaining following substantial depletion is typically from about 0% to about 30% by volume, preferably from about 10% to about 30% by volume.

The terms "non-red blood cell-depleted" and "red blood cells are not depleted" as used herein refer to processed umbilical cord blood units in which a volume of red blood cells less than about 30%, 25,%, 20%, 15%, 10%, 5%, 4%, 3%, 2%, or 1% has been removed.

As used herein, the terms "red blood cell is substantially depleted" and "red blood cell-depleted" refer to processed umbilical cord blood units in which a volume of red blood cells greater than about 30%, 35%, 40%, 45%, 50%, 55%, 60%, 65%, 70%, 75%, 80%, 85%, 90%, or 95% has been removed.

"Nucleated cells" refers to cells that have a nucleus, i.e., an organelle that comprises chromosomal DNA. Nucleated cells include, e.g., white blood cells and stem cells. "Unnucleated cells" includes, e.g., adult red blood cells.

The term "lithium salt" refers to any pharmaceutically acceptable salt of lithium. Examples of lithium salts suitable for use in the methods of the present invention include, but are not limited to, lithium chloride, lithium carbonate, and lithium sulfate, lithium citrate, lithium oxybutyrate, lithium orotate, lithium acetate, lithium aluminate, lithium aluminium hydride, lithium amide, lithium borate, lithium bromide, lithium diisopropylamide, lithium fluoride, lithium hydride, lithium hydroxide, lithium iodide, lithium metaborate, lithium molybdate, lithium niobate, lithium nitrate, lithium nitride, lithium oxide, lithium perchlorate, lithium peroxide, lithium sulfide, lithium tantalate, lithium gamma-linolenate, and combinations thereof. Preferably, the lithium salt is lithium chloride.

The term "subject" refers to a mammal such as a human.

As used herein, the term "administering" refers to the delivery of stem cells such as human umbilical cord blood cells or a lithium salt such as lithium chloride by any route including, without limitation, oral, intranasal, intraocular, intravenous, intraosseous, intraperitoneal, intraspinal, intramuscular, intra-articular, intraventricular, intracranial, intralesional, intratracheal, intrathecal, subcutaneous, intradermal, transdermal, or transmucosal administration. The lithium salt is typically administered via an oral, intrathecal, intraventricular, subcutaneous, intraperitoneal, intravenous, or intramuscular route. In certain instances, the lithium salt is administered by an osmotic pump implanted in a subject using, e.g., a DUROS® Implant available from Alza Corp. (Mountain View, Calif.). In certain other instances, the lithium salt is administered by a sustained release depot injection. The stem cells can be administered, for example, by direct injection or infusion into a disease site, an injury site (e.g., intraspinal administration for treatment of a spinal cord injury), or other target site such as an organ. The stem cells and lithium salt can be administered simultaneously (e.g., at the same time) or sequentially (e.g., over the course of several minutes, hours, or days) to a subject.

III. Umbilical Cord Blood Stem Cells

A. Collection of Umbilical Cord Blood

Umbilical cord blood is a rich source of stem cells and can be obtained easily and without trauma to the donor. In contrast, the collection of bone marrow cells for transplantation is a traumatic experience which is costly in terms of time and money spent for hospitalization. Preferably, umbilical cord blood is collected by direct drainage from the umbilical cord. As such, following delivery of the infant, the umbilical cord can be doubly cross-clamped and transected just above the crushed portion in the clamp, and the resulting flow of fetal blood from umbilical vessels can be caught in a collection vessel. An adequate collection can usually be accomplished without milking the cord and is complete in approximately two minutes, before placental separation has occurred. Care should be taken to avoid contamination by maternal blood, urine, or other fluids in the delivery field. Umbilical cord blood can also be obtained by any other method known in the art.

A donor for the purposes of the present invention may include maternal donors who are donors for the purpose of informed consent for the donation, and are mothers with custodial rights of the actual newborn donors, with the actual donors of umbilical cord blood being the newborn babies. Maternal donors are individuals who are in good general health and between the ages of about 16 and about 50. Certain information may be collected from the maternal donor before or after cord blood donation in order to determine donor suitability and lack of transfusion transmitted infectious diseases, genetic diseases, and cancers of the hematopoietic system. For example, the maternal donor may be given a medical questionnaire to fill out. In one embodiment of the present invention, a maternal donor will undergo a medical examination before donation.

Collection of umbilical cord blood should be made under sterile conditions. In some embodiments, the cord blood can be mixed with an anticoagulant immediately upon collection. Generally, from about 23 ml to about 35 ml of the anticoagulant is mixed with up to about 255 ml of cord blood (i.e., one cord blood unit). Suitable anticoagulants include any known in the art, such as, e.g., CPDA (citrate-phosphate-dextrose-adenosine), CPD (citrate-phosphate-dextrose), ACD (acid-citrate-dextrose), Alsever's solution (Alsever et al., *N. Y. St. J. Med.*, 41:126 (1941)), De Gowin's Solution (De Gowin et al., *J. Am. Med. Assoc.*, 114:850 (1940)), Edglugate-Mg (Smith et al., *J. Thorac. Cardiovasc. Surg.*, 38:573 (1959)), Rous-Turner Solution (Rous et al., *J. Exp. Med.*, 23:219 (1916)), other glucose mixtures, heparin, ethyl biscoumacetate, etc.

To aid cord blood processing and improve safety, processing bags for various blood components may be part of a sterile blood bag system. In one embodiment, a plasma storage solution may be incorporated into one of the processing bags. Additionally, both the collection bag and the processing bags may be equipped with ports and break connectors. The ports may be used for the addition or extraction of materials to or from the inside of the bag. A break connector may be used to temporarily close a tube or the entrance of a bag.

The cord blood can typically be stored at temperatures, e.g., between about 0° C. and about 42° C. or between about 15° C. and about 26° C., for up to about 48 hours.

In addition to umbilical cord blood, placental or fetal blood can be used to obtain stem cells that are suitable for culturing and/or transplantation. Placental or fetal blood can be collected by any method known in the art. For example, fetal blood can be taken from the fetal circulation at the placental root with the use of a needle guided by ultrasound, placentocentesis, or fetoscopy. Placental blood can be obtained, e.g., by needle aspiration from the delivered placenta at the root and at distended veins.

In some embodiments, postnatal women are asked to donate cord blood and placental blood. Hospitals are contacted and asked to participate in a umbilical cord/placental blood collection project. Potential donors are women who are in labor and are about to deliver a baby either by natural delivery or Cesarean section. In U.S. Pat. No. 5,993,387, one method of obtaining umbilical cord blood and placental blood from postnatal women is described, e.g., by enrolling a family with a bank before a child is born and collecting a fee for the collection and storage of the cord stem cells to be collected after birth.

In one embodiment, after delivery, the cord blood and/or placenta is collected and examined. In some embodiments, examination ensures that the cord blood or placental blood is suitable for further processing. An examination may include examining the placenta to make sure it is intact and free from heavy meconium or purulent discharge. The umbilical cord may be examined to determine that it is intact with 2 arteries and 1 vein and devoid of true knots or other abnormalities. As described above, collection can be into a bag that optionally contains an anticoagulant such as a citrate-phosphate-dextrose-adenosine (CPDA) solution.

B. Plasma Depletion Processing

In some embodiments, the volume of collected cord blood can be reduced according to the process described in, e.g., U.S. Patent Publication No. 20060275271. As a non-limiting example, volume reduction of collected cord blood can be performed by first centrifuging the mixture at temperatures between about 0° C. and about 42° C., preferably about between 15° C. and about 26° C. The centrifugation is done to remove a substantial volume of liquid, e.g., plasma, from the mixture. The centrifugation is preferably performed at about 1,000×g to about 2,500×g for between about 5 and about 20 minutes, with the centrifugal force and centrifugation time sufficient to cause sedimentation of most of the cells without causing cell damage. After centrifugation, a substantial volume of plasma is removed to reduce the volume of the cord blood mixture to produce a plasma-depleted cord blood unit that has not been depleted of red blood cells. The plasma volume remaining following substantial depletion is typically from about 0% to about 30% by volume, preferably from about 10% to about 30% by volume. In certain instances, at least about 10 ml of plasma is left in the plasma-depleted cord blood unit. Preferably, less than about 5% of the nucleated cells (e.g., less than about 5%, 4%, 3%, 2%, or 1%) are lost when the supernatant is removed, as evidenced by enumeration of cells in the supernatant plasma.

In some embodiments, the plasma-depleted unit is transferred to a freezing container, e.g., a Cryocyte® bag, and cooled to between about 2° C. and about 8° C. for about 30 to about 60 minutes. The acceptable volume is determined by the holding volume of the particular CryoCyte® bag used, the number of cells to be cryopreserved, and the concentration of the cryopreservant solution. If the volume of the plasma-depleted cord blood unit is too large as to cause the volume to exceed about 60 or about 75 ml, then a larger CryoCyte® bag can be used or the sample can be divided among two or more CryoCyte® bags.

C. Culturing Cord Blood Stem Cells

The stem cells present in an umbilical cord blood unit can be cultured using an in vitro culture technique in a medium comprising a lithium salt either before or after cryopreservation. Various protocols have been described for the growth of cord blood stem cells in culture (see, e.g., Smith et al., *Br. J. Haematol.*, 63:29-34 (1986); Dexter et al., *J. Cell. Physiol.*, 91:335 (1977); Witlock et al., *Proc. Natl. Acad. Sci. U.S.A.*, 79:3608-3612 (1982)). One skilled in the art will know of other protocols for culturing the population of cord blood stem cells in vitro.

Various factors can be used in conjunction with a lithium salt for stimulating the proliferation of cord blood stem cells in culture. As non-limiting examples, a variety of cytokines and growth factors such as interleukin-1 (IL-1), interleukin-3 (IL-3), interleukin-4 (IL-4), interleukin-6 (IL-6), and granulocyte macrophage-colony stimulating factor (GM-CSF) can be used in combination with a lithium salt to stimulate the ex vivo expansion of stem cells present in the umbilical cord blood unit.

Cord blood stem cells cultured by the methods of the present invention can be used without further purification. Alternatively, a specific population or subpopulation of cultured stem cells can be isolated by various techniques known in the art, such as immunoaffinity chromatography, immunoadsorption, FACS sorting, and the like. As a non-limiting example, cord blood stem cells can be isolated based on their expression of cell-surface markers such as CD34, c-kit, and/or CXCR-4.

The present invention relies upon routine techniques in the field of cell culture. Suitable cell culture methods and conditions can be determined by those of skill in the art using known methodology (see, e.g., Freshney et al., CULTURE OF ANIMAL CELLS, 3rd ed. (1994)). In general, the cell culture environment includes consideration of such factors as the substrate for cell growth, cell density and cell contract, the gas phase, the medium, and temperature.

Incubation is generally performed under conditions known to be optimal for cell growth. Such conditions may include, for example, a temperature of about 37° C. and a humidified atmosphere containing about 5% $CO_2$. The duration of the incubation can vary widely, depending on the desired results. Proliferation can be conveniently determined using $^3H$ thymidine incorporation or BrdU labeling.

Plastic dishes, flasks, roller bottles, or microcarriers in suspension may be used to culture cord blood stem cells according to the methods of the present invention. Suitable culture vessels include, for example, multi-well plates, petri dishes, tissue culture tubes, flasks, roller bottles, and the like. Cord blood stem cells are typically grown at optimal densities that are determined empirically based on the cell type and passaged when the cell density is above optimal.

Cultured cord blood stem cells are normally grown in an incubator that provides a suitable temperature, e.g., the body temperature of the animal from which the cells were obtained, accounting for regional variations in temperature. Generally, 37° C. is the preferred temperature for cell culture. Most incubators are humidified to approximately atmospheric conditions.

Important constituents of the gas phase are oxygen and carbon dioxide. Typically, atmospheric oxygen tensions are used for cell cultures. Culture vessels are usually vented into the incubator atmosphere to allow gas exchange by using gas permeable caps or by preventing sealing of the culture vessels. Carbon dioxide plays a role in pH stabilization, along with buffer in the cell media and is typically present at a concentration of from about 1% to about 10% in the incubator. The preferred $CO_2$ concentration typically is about 5%.

Defined cell media are available as packaged, premixed powders or presterilized solutions. Examples of commonly used media include, but are not limited to, Dulbecco's Modification of Eagle's Medium (DMEM), DME, RPMI 1640, Iscove's complete media, and McCoy's Medium (see, e.g., GibcoBRL/Life Technologies Catalog and Reference Guide; Sigma Catalog). Defined cell culture media are supplemented with a lithium salt, e.g., lithium chloride, at about 0.5-5 mM, e.g., about 0.5, 1, 1.5, 2, 2.5, 2.6, 2.7, 2.8, 2.9, 3, 3.1, 3.2, 3.3, 3.4, 3.5, 4, 4.5, or 5 mM. In some embodiments, the lithium salt is present at about 3 mM. Defined cell culture media can also be supplemented with about 5-20% serum, typically heat inactivated serum, e.g., human, horse, calf, and fetal bovine serum. Typically, 10% fetal bovine serum (FBS) or human serum (HS) is used in the methods of the present invention. The culture medium is usually buffered to maintain the cells at a pH of from about 7.2-7.4. Other supplements to the media include, e.g., antibiotics, amino acids, sugars (e.g., glucose at about 5.5-16.7 mM), and growth factors (e.g., EGF, FGF, and the like).

IV. Administration of Cultured Stem Cells and Lithium Salts

Lithium salts and stem cells cultured according to the methods of the present invention may be administered to a subject by any means known in the art. Suitable means of administration include, for example, intravenous or subcutaneous administration, or local delivery, e.g., direct injection or infusion into a disease site, an injury site, or other target site such as an organ.

The cultured stem cells and lithium salts described herein can be administered either alone or in a mixture with a pharmaceutically acceptable carrier. Pharmaceutically acceptable carriers are determined in part by the particular composition being administered (e.g., cells, salts, etc.), as well as by the particular method used to administer the composition. Accordingly, there are a wide variety of suitable pharmaceutical formulations for administering the cultured cells and lithium salts of the present invention. As a non-limiting example, normal buffered saline (e.g., about 135-150 mM NaCl) can be employed as the pharmaceutically acceptable carrier. Other suitable carriers include, but are not limited to, water, buffered water, 0.4% saline, 0.3% glycine, and the like. Additional suitable carriers are described in, e.g., REMINGTON'S PHARMACEUTICAL SCIENCES, Mack Publishing Co., Philadelphia, Pa., 18th ed. (1995). As used herein, the term "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically acceptable" refers to molecular entities and compositions that do not produce an allergic or similar untoward reaction when administered to a mammal such as a human.

The stem cells and lithium salts of the present invention may be in formulations suitable for administration, such as, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Injection solutions and suspensions can be prepared from sterile powders, granules, and tablets. The dose administered to a subject, in the context of the present invention, should be sufficient to effect a beneficial therapeutic response in the subject over time. With regard to cultured stem cells, the dose will be determined by the efficacy of the particular stem cells employed and the condition of the subject, as well as the body weight or surface area of the subject to be treated. The size of the dose will also be determined by the existence, nature, and extent of any adverse side-effects that accompany the administration of a particular cell type in a particular subject. With regard to lithium salts, the dose will be determined by the efficacy of the particular lithium salt employed and the condition of the subject, as well as the body weight or surface area of the subject to be treated. The size of the dose will also be determined by the existence, nature, and extent of any adverse side-effects that accompany the administration of a particular lithium salt in a particular subject.

In determining the effective amount of the cultured stem cells to be administered in the treatment of a disease or injury described herein, a physician evaluates cell toxicity, transplantation reactions, progression of the disease, and the production of anti-cell antibodies. For administration, the cultured stem cells of the present invention can be administered in an amount effective to diminish or relieve one or more symptoms associated with the disease or injury, taking into account the side-effects of the cell type at various concentrations, as applied to the mass and overall health of the subject. Administration can be accomplished via single or divided doses.

In some embodiments, the present invention provides a method for treating a subject suffering from a disease or disability (e.g., spinal cord injury) comprising administering to the subject stem cells collected, processed, and/or cultured according to the methods described herein. As a non-limiting example, the lithium-stimulated stem cells can be administered to a subject in an amount sufficient to replenish cells lost due to disease or injury.

In certain instances, the cells to be replaced due to illness or disease are blood cells. Alternatively, subjects undergoing chemotherapy or radiation therapy for cancer may have their bone marrow cells destroyed by such therapy, thus leading to an increased susceptibility of developing various infectious diseases. These subjects can also be treated with stem cells derived from the methods of the present invention. In certain other instances, the stem cells may be used to treat subjects suffering from spinal cord injury, traumatic brain injury, stroke, Parkinson's disease, Alzheimer's disease, burns, heart disease, diabetes, osteoarthritis, rheumatoid arthritis, etc. The stem cells can also be used to treat subjects suffering from a disease such as leukemia, lymphoma, anemia, multiple myeloma, inherited blood disorders, and diseases or treatments resulting in an immunodeficiency (e.g., AIDS).

The stem cells can be administered to a subject alone or in conjunction with other therapeutic regimens. In certain instances, the additional therapeutic regimen comprises chemotherapy and/or radiation therapy. In certain other instances, the additional therapeutic regimen comprises at least one growth factor such as, for example, GM-CSF, G-CSF, M-CSF, IL-3, IL-7, EPO, TPO, IL-5, or any of the other growth factors described herein. The treatments may be administered simultaneously or sequentially.

V. Stem Cell Transplantation

In some embodiments, stem cells are transplanted without HLA typing. In other embodiments, stem cells are HLA typed to ensure compatibility with the recipient. The number of matches of HLA markers depends on the needs of the user and the source of the stem cells. For example, stem cells that have been isolated from embryonic or fetal tissue, including cord blood, can be used with four of six, five of six, or six of six marker matches. Stem cells from adults are preferably used when six of six HLA markers are compatible. In some immunocompromised subjects, graft versus host response can be attenuated and stem cells that are not perfectly matched can be used.

Typically, the normal stem cell population present in the subject is eliminated or reduced prior to transplantation of the therapeutic stem cell units. Chemotherapy, radiation, or the techniques described in, e.g., U.S. Pat. No. 6,217,867 can be used to condition the bone marrow for appropriate engraftment of the transplant. Finally, therapeutic stem cell units can be transplanted into the patient using standard methods.

In some embodiments, stem cells are transplanted with a pharmaceutically acceptable carrier, preferably an aqueous carrier. A variety of aqueous carriers can be used, e.g., buffered saline and the like. These solutions are sterile and generally free of undesirable matter. The therapeutic stem cell unit may also contain pharmaceutically acceptable auxiliary substances as required to approximate physiological conditions, such as pH adjusting and buffering agents, toxicity adjusting agents and the like, for example, sodium acetate, sodium chloride, potassium chloride, calcium chloride, sodium lactate, albumin, dextran, DMSO, combinations thereof, and the like. The concentration of auxiliary substances can vary widely, and will be selected primarily based on fluid volumes, viscosities, body weight, and the like in accordance with the particular mode of administration selected and the subject's needs.

VI. Examples

The present invention will be described in greater detail by way of the following examples. The following examples are offered for illustrative purposes, and are not intended to limit the present invention in any manner. Those of skill in the art will readily recognize a variety of noncritical parameters which can be changed or modified to yield essentially the same results.

Example 1. Lithium Stimulation of Rat Neonatal Blood Cell Proliferation and Growth Factor Production This example illustrates that lithium promotes the proliferation and growth factor production of stem cells isolated from neonatal rat blood (N01.1 cells). Lithium also enhances the survival and growth of transplanted N01.1 cells.

Results

In Vitro.

FIG. 1 shows that lithium promotes N01.1 cell proliferation in vitro. N01.1 cells were cultured in growth medium containing 3 mM lithium chloride for 7 days. Cell number was counted for both groups. The number of cells in the lithium chloride group was 359% higher than the control group. Lithium-treated N01.1 cells were still Nestin positive.

Figure 2:
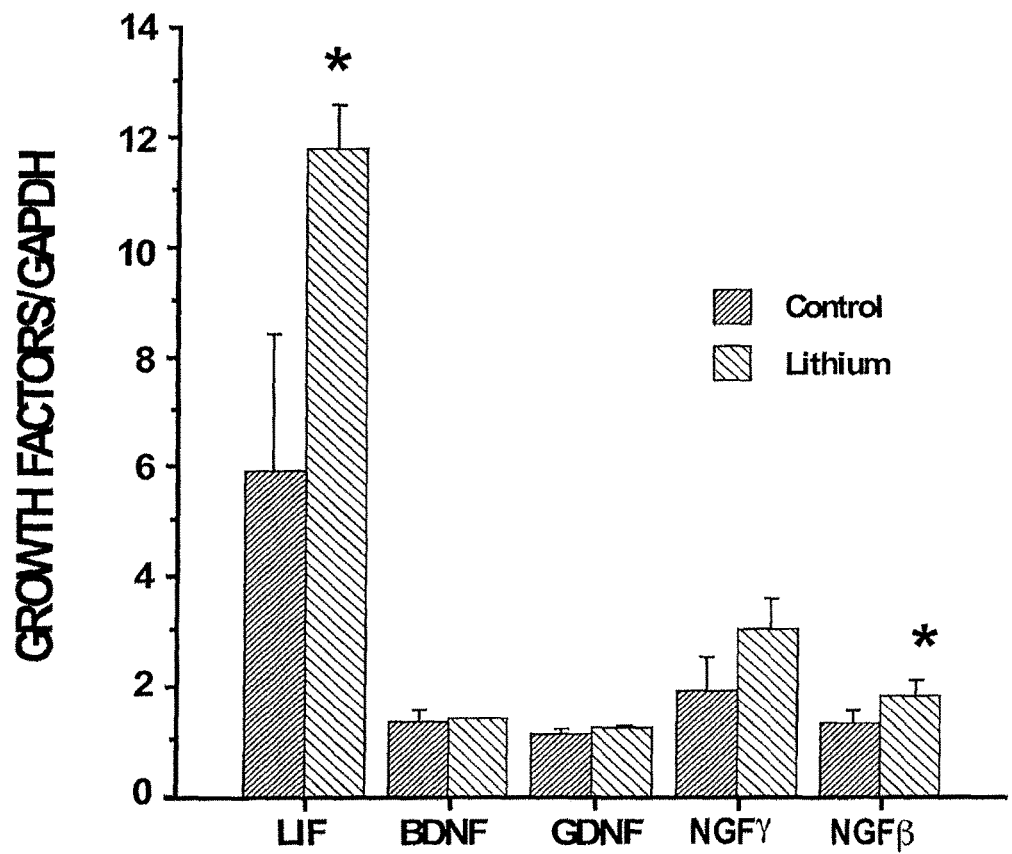
FIG. 2 illustrates data demonstrating that lithium stimulates N01.1 cell growth factor production in vitro.

FIG. 2 shows that lithium stimulates N01.1 cell growth factor production in vitro. The mRNA levels of growth factors such as LIF, BDNF, GDNF, NGFγ, and NGFβ in N01.1 cells cultured with or without 3 mM lithium chloride was determined using quantitative real-time PCR. LIF and NGFβ mRNA levels were significantly greater than the control group. There were no significant differences between the mRNA levels of NGFγ, BDNF, and GDNF.

In Vivo.

GFP-positive N01.1 cells were transplanted immediately after a 25 mm height weight drop contusion. The rats were injected with 100 mg/kg lithium chloride intraperitoneally daily for 2 weeks. The control group was injected with saline daily for 2 weeks. Animals were sacrificed at 2 weeks for RT-PCR and histological analysis.

Figure 3:
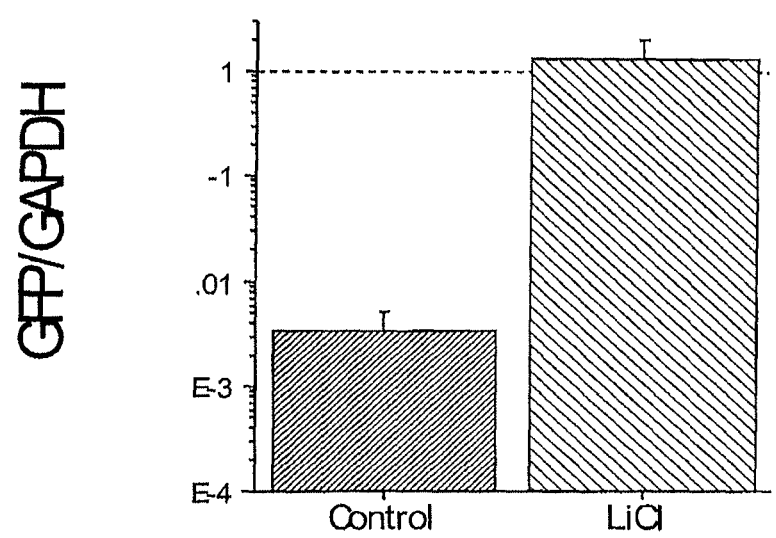
FIG. 3 illustrates data demonstrating that lithium promotes N01.1 cell proliferation in vivo as determined by quantitative real-time PCR.
Figure 4:
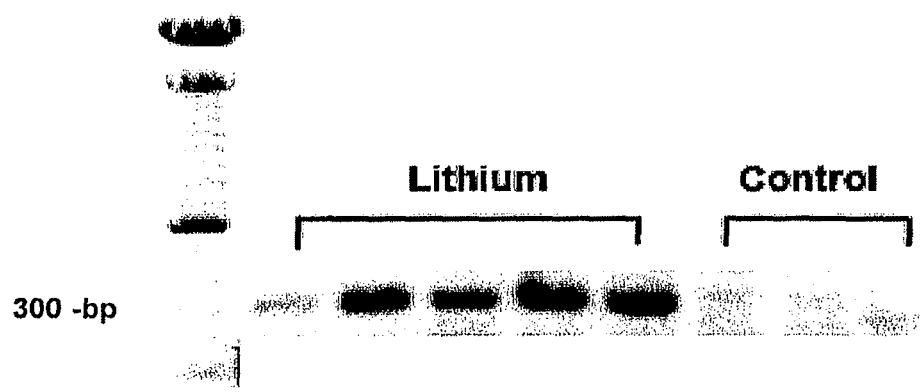
FIG. 4 illustrates data demonstrating that lithium promotes N01.1 cell proliferation in vivo as determined by genomic PCR.

FIGS. 3 and 4 show that lithium promotes N01.1 cell proliferation in vivo. In FIG. 3, the level of GFP mRNA in the spinal cord at 2 weeks after N01.1 cell transplantation with saline or lithium treatment was determined by quantitative real-time PCR. In saline-treated rats, the amount of GFP mRNA was detectable, but very low. In lithium-treated rats, however, the amount of GFP mRNA was 1000× greater than that observed in saline-treated rats. In FIG. 4, genomic DNA of transplanted spinal cord tissue was isolated and genomic PCR analysis was performed with a GFP primer set. In lithium-treated tissues, the amount of amplified GFP DNA was significantly greater than that observed in the control group.

Figure 5:
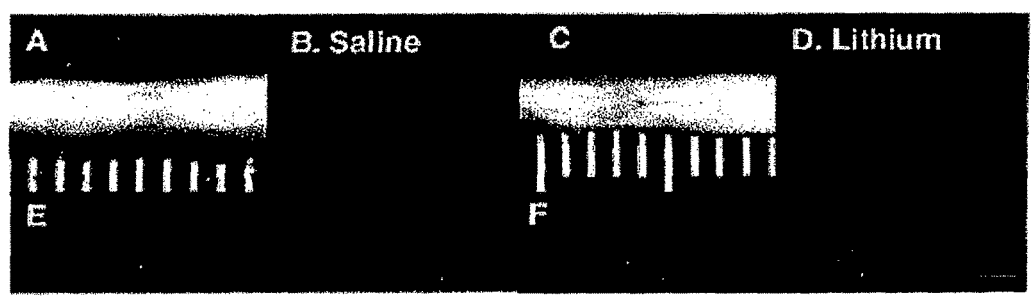
FIG. 5 illustrates data demonstrating that lithium promotes N01.1 cell survival in vivo as determined by histological analysis. Left, rostral; Right, caudal. Scale=1 mm.

FIG. 5 shows that lithium promotes N01.1 cell survival in vivo. GFP-positive N01.1 cells were transplanted into injured rat spinal cords. After 2 weeks, rats were perfused and spinal cords were observed under a Zeiss Stemi dissecting microscope. In saline-treated rats, GFP fluorescence intensity was low and diffuse (FIGS. 5A-B). In lithium-treated rats, however, GFP fluorescence intensity was high and occupied two large areas (FIGS. 5C-D). To further evaluate the distribution of GFP-N01.1 cells, the same spinal cords were sectioned sagittally. In saline-treated rats, GFP-positive N01.1 cells were sparse (FIG. 5E). In contrast, lithium-treated rats had a large number of GFP-positive N01.1 cells at the contusion center (FIG. 5F).

Figure 6:
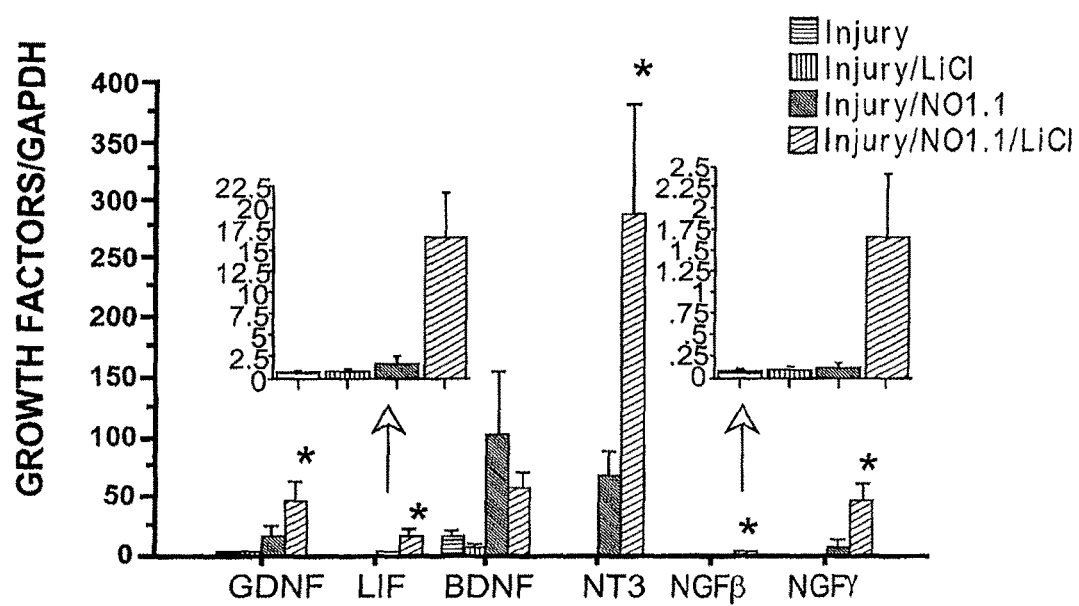
FIG. 6 illustrates data demonstrating that lithium stimulates N01.1 cell growth factor production in vivo.

FIG. 6 shows that lithium stimulates N01.1 cell growth factor production in vivo. To investigate the effect of lithium on growth factor production, four groups of spinal cords were analyzed by quantitative real-time PCR. In the "Injury" and "Injury/LiCl" groups, there were no significant changes in growth factor mRNA levels. In the "Injury/N01.1" group, BDNF, NT3, and NGFγ mRNA levels were elevated. In the "Injury/N01.1/LiCl" group, there were significant increases in GDNF, LIF, BDNF, NT-3, NGFβ, and NGFγ mRNA levels. These results demonstrate that lithium stimulates growth factor production in the presence of N01.1 cells.

Figure 7:
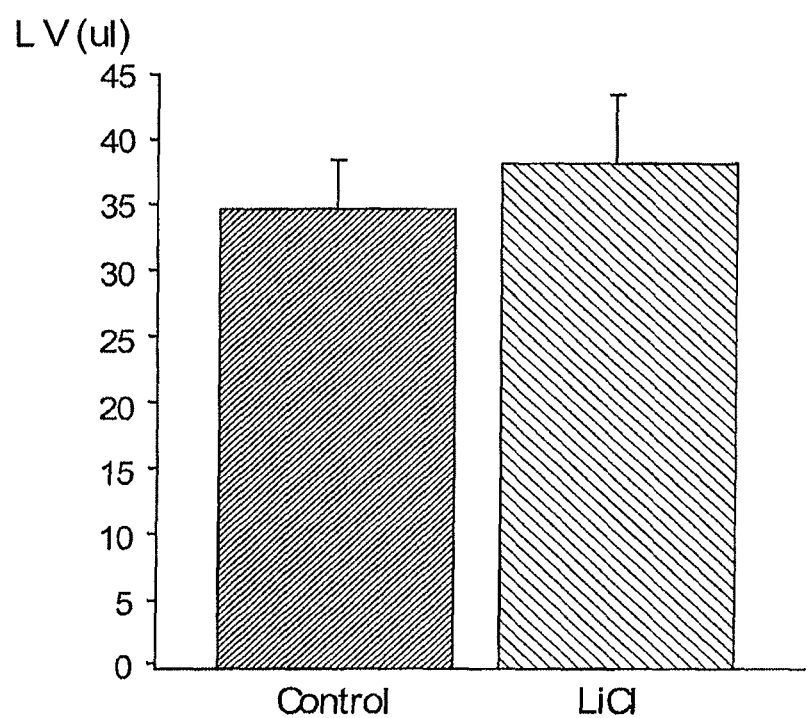
FIG. 7 illustrates data demonstrating the effect of lithium on neuroprotection following spinal cord injury.

FIG. 7 shows the effect of lithium on neuroprotection following spinal cord injury. Lithium chloride or saline was injected (ip) soon after spinal cord injury. Lesion volumes were measured 24 hrs after injury. No significant difference between lithium-treated and saline-treated rats was observed.

Discussion

The effects of lithium on stem cell proliferation, gene expression, and tissue protection after spinal cord injury were examined. Using a nestin-expressing cell line (N01.1) isolated from neonatal rat blood that was transfected with green fluorescent protein (GFP), the effects of lithium on N01.1 cell proliferation in culture and N01.1 cells implanted into injured spinal cords were determined. Incubating N01.1 cells in 3 mM lithium resulted in a 359% increase in the number of cells after 1 week. When N01.1 cells were transplanted into rat spinal cord after a 25-mm contusion injury, they did not grow out of control and respected the gray-white matter boundaries of the spinal cord. At 2 weeks after transplantation, the transplantation site was assayed for GFP mRNA levels. In saline-treated rats, GFP mRNA was detectable, but very low. In lithium-treated rats, however, the amount of GFP mRNA was 1000× greater than that in saline-treated rats. Histology also showed more GFP-positive cells in the injured spinal cord with lithium treatment. The amount of mRNA of growth factors such as GDNF, LIF, BDNF, NT-3, NGFβ, and NGFγ were also greater in lithium-treated rats. As such, this example demonstrates that lithium is useful for enhancing the survival and growth of transplanted stem cells by promoting cell proliferation and stimulating growth factor expression in vivo. It is thus ideal for combination therapy in patients that have received stem cell transplants.

Methods

Cell Character.

N01 cells were isolated from the blood of wild-type neonatal (P0) Sprague-Dawley (SD) rats and cultured with DMEM, 10% FBS, EGF, and bFGF. At 6 weeks, 60% of N01 cells were Nestin positive. After a clonal assay. a subclone named N01.1 having 100% Nestin positivity was selected. N01.1 cells can be cultured for a long period of time without any change in morphology or Nestin marker. When serum was withdrawn from growth media, N01.1 cells formed spherical structures that were similar to neurospheres formed by neural stem cells (Sun, 1st Annual Scientific Meeting on Stem Cell Research in New Jersey, 2004).

In Vitro Culture.

N01.1 cells were treated with 3 mM lithium chloride for 7 days in DMEM, 10% FBS, bFGF, and EGF at 37° C., 5% $CO_2$ humidified chamber.

In Vivo Spinal Cord Injury/Cell Transplantation.

N01.1 cells were transfected with green fluorescent protein (GFP). 77+1 day old SD rats were used. A contusion (MASCIS impactor, 25 mm height) was made, and shortly thereafter a total of 200,000 cells was injected intraspinally with a glass micropipette attached to a Hamilton syringe at two sites that were 2 mm apart from the contusion site (100,000 cells/μl).

In Vivo Lithium Treatment.

Lithium chloride was administered intraperitoneally at 100 mg/kg per injection/day, every day for 2 weeks.

Quantitative Real-Time PCR.

To evaluate the cell survival of implanted GFP-positive N01.1 cells 2 weeks after transplantation, the amount of GFP mRNA was measured by SYBR green fluorescence on an Applied Biosystems 7900HT Real-Time PCR System (Foster City, Calif.). The mRNA levels of LIF, BDNF, NT3, GDNF, NGFγ, and NGFβ in the spinal cord following N01.1 cell transplantation were measured.

Lesion Volume (LV).

To evaluate the effect of lithium on tissue protection, lesion volumes were measured 24 hrs after injuries according to the following formula: $LV=0.75-([K]t-4)/120 \times$ weight (Constantini et al., *J. Neurosurg.*, 80:97-111 (1994)).

Example 2. Lithium Stimulation of Human Umbilical Cord Blood Cell Proliferation and Growth Factor Production This example illustrates that lithium promotes the proliferation and growth factor production of stem cells isolated from human umbilical cord blood.

Figure 8:
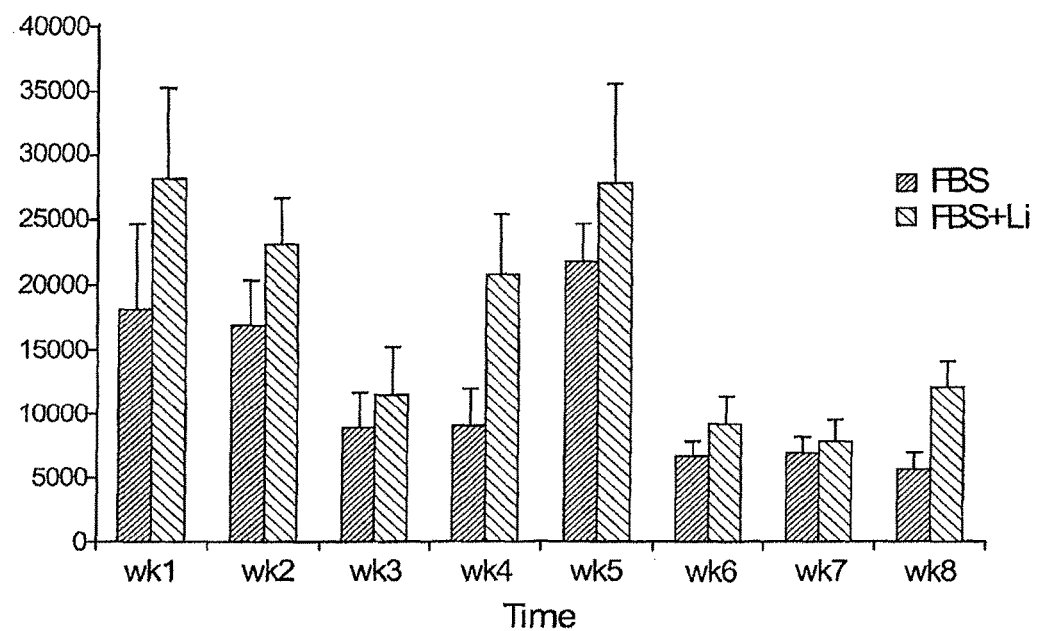
FIG. 8 illustrates data demonstrating that lithium promotes human umbilical cord blood cell proliferation in vitro.

FIG. 8 shows that lithium promotes human umbilical cord blood cell proliferation in vitro. Human mononuclear cells were isolated from fresh human umbilical cord blood and cultured in growth media containing fetal bovine serum (FBS) with or without 3 mM lithium chloride. In lithium-treated cultures, the cell number was higher than in control cultures during the length of the 8-week study. Although the total cell number decreased in both lithium-treated and control cultures after 5 weeks, there were significantly more cells in lithium-treated cultures at week 8.

Figure 9:
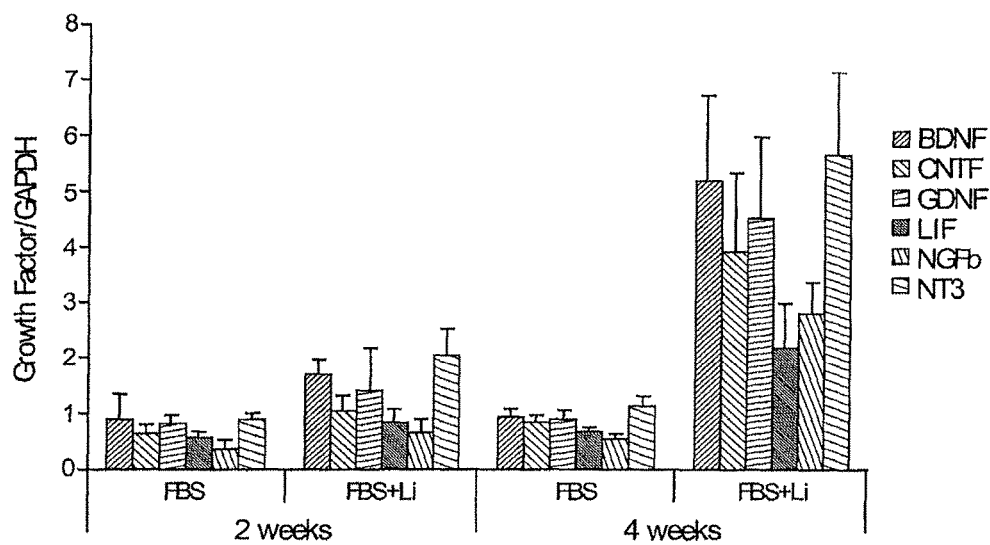
FIG. 9 illustrates data demonstrating that lithium stimulates human umbilical cord blood cell growth factor production in vitro.

FIG. 9 shows that lithium stimulates growth factor production in vitro. Human mononuclear cells were isolated from fresh human umbilical cord blood. Cells were cultured in growth media containing FBS with or without 3 mM lithium chloride. Quantitative real-time PCR was performed at 2 and 4 weeks to evaluate growth factor mRNA levels. At 4 weeks, lithium-treated cultures had a 2-5 fold increase in growth factor mRNA levels (e.g., GDNF, LIF, BDNF, NT-3, NGFβ, and CNTF) compared to control cultures.

Figure 10:
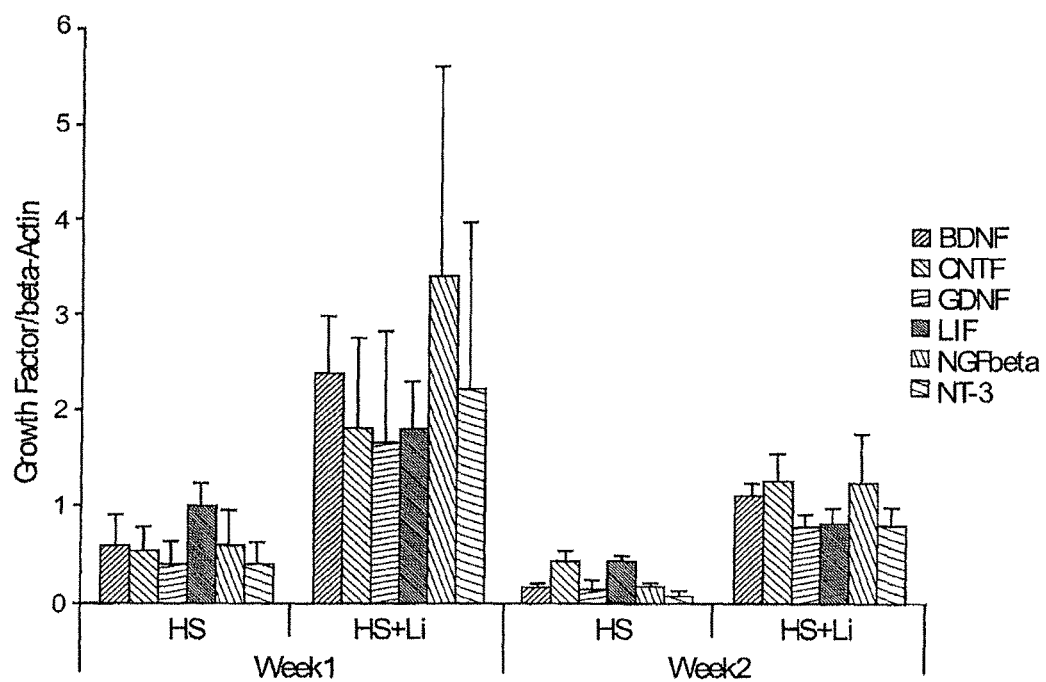
FIG. 10 illustrates additional data demonstrating that lithium stimulates human umbilical cord blood cell growth factor production in vitro.

FIG. 10 shows that lithium stimulates growth factor production in vitro. Human mononuclear cells were isolated from fresh human umbilical cord blood. Cells were cultured in growth media containing adult human serum (HS) with or without 3 mM lithium chloride (Li). Quantitative real-time PCR was performed at 1 and 2 weeks to evaluate growth factor mRNA levels. At both time points, lithium-treated cultures showed a significant increase in growth factor mRNA levels (e.g., BDNF, CNTF, GDNF, LIF, NGFβ, and NT-3) compared to control cultures.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

What is claimed is:

1. A method for enhancing survival and growth of transplanted human umbilical cord blood cells in a subject, said method comprising:
   (a) culturing human umbilical cord blood cells in a medium comprising a lithium salt;
   (b) administering the cells of step (a) to a subject; and
   (c) administering a lithium salt to said subject.

2. The method of claim 1, wherein said lithium salt is selected from the group consisting of lithium chloride, lithium carbonate, and lithium sulfate.

3. The method of claim 1, wherein said lithium salt is present in said medium at a concentration of from about 0.5 to about 5 mM.

4. The method of claim 1, wherein said subject has been diagnosed with a spinal cord injury.

5. The method of claim 1, wherein said cells are administered intraspinally.

6. The method of claim 1, wherein said lithium salt is administered by a route selected from the group consisting of oral, intrathecal, intraventricular, subcutaneous, intraperitoneal, intravenous, and intramuscular.

* * * * *